United States Patent

Kamuro et al.

[11] Patent Number: 4,619,685
[45] Date of Patent: Oct. 28, 1986

[54] PROCESS FOR CONTROLLING THE GROWTH OF SUCKERS ON A TOBACCO PLANT

[75] Inventors: Yasuo Kamuro, Urawa; Koichi Hirai, Hanyu; Fumio Suzuki; Susumu Yamamoto, both of Funabashi; Noboru Shindo, Machida, all of Japan

[73] Assignee: Nissan Chemical Industries, Ltd., Tokyo, Japan

[21] Appl. No.: 671,689

[22] Filed: Nov. 15, 1984

[30] Foreign Application Priority Data

Nov. 18, 1983 [JP] Japan .................. 58-217166

[51] Int. Cl.$^4$ .............................. A01N 37/44
[52] U.S. Cl. .................................. 71/78; 71/111; 71/114; 560/43; 562/456; 260/501.15
[58] Field of Search ................ 560/43; 71/78, 111

[56] References Cited

U.S. PATENT DOCUMENTS 4,102,671 7/1978 Haddock et al. ............... 71/111
4,267,355 5/1981 Scott et al. ..................... 71/111

FOREIGN PATENT DOCUMENTS 57-116003 7/1982 Japan ............................. 71/111

Primary Examiner—Natalie Trousof
Assistant Examiner—Bruce D. Gray
Attorney, Agent, or Firm—Quaintance, Murphy & Presta

[57] ABSTRACT

A plant growth regulator comprising, as the active substance, one or more of N-substituted alanine derivatives of the general formula:

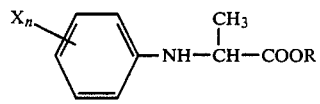

wherein X represents halogen atom or trifluoromethyl, R represents hydrogen, straight chain or branched chain alkyl having 1–4 carbon atoms, alkenyl having 2–4 carbon atoms, an alkali metal atom or amine-forming residue, and n is zero or an integer of 1 or 2, with the proviso that when n is 2, X may be same or different, together with an inert carrier or diluent, in particular, an agent effective for controlling suckers of tobacco, and a process for regulating plant growth by using said plant growth regulator.

13 Claims, No Drawings

PROCESS FOR CONTROLLING THE GROWTH OF SUCKERS ON A TOBACCO PLANT

BACKGROUND OF THE INVENTION

The present invention relates to a plant growth regulator containing as the active substance one or more N-substituted alanine derivatives, especially an agent which is effective to control suckers of tobacco plant.

Some of the N-substituted alanine derivatives to be used as the active substances in the present invention are novel and others are known compounds. It has been known that some N-substituted alanine derivatives are useful as herbicidally active substances as disclosed in Japanese Patent Laid-open specification Sho No. 52-15821 (corresponding to British Pat. No. 1547758) and U.S. Pat. No. 4,102,671. However, it has not heretofore been known that the derivatives are useful as agents for controlling suckers of tobacco and young shoots of woody plants.

Most of the compounds of the present invention have strong auxin activities. It has been known that when a compound having strong auxin activity is applied to plants, abnormal growth, serious malformation, or withering actions are often exhibited. Therefore, the compounds are generally used as herbicides for killing undesirable weeds.

It has been unexpectedly found that some compounds which have strong auxin activities can effectively control young shoots of woody plants and suckers of tobacco plant while causing substantially no adverse effect on the plant growth and the yield of tobacco in practical use, thus the present invention has been accomplished.

SUMMARY OF THE INVENTION

The object of the present invention is to offer a useful plant growth regulator.

A further object of the present invention is to offer a plant growth regulator which can inhibit growth of new shoots of woody plants without causing any adverse influence on the plant growth and the crop yield.

Another object of the present invention is to provide a lateral buds inhibiting agent which can control lateral buds of tobacco plant.

Furthermore, another object of the present invention is to offer a process for controlling shooting of lateral buds of woody plants.

A further object of the present invention is to offer novel N-substituted alanine derivatives which have useful plant growth regulating activities.

The present invention provides a plant growth regulator comprising, as the active substance, N-substituted alanine derivatives of the general formula:

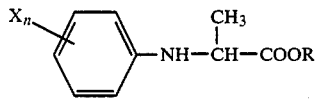

wherein X represents halogen atom or trifluoromethyl, R represents hydrogen, straight chain or branched chain alkyl group having 1-4 carbon atoms, alkenyl having 2-4 carbon atoms, an alkali metal atom or an amine-forming residue and n is zero or an integer of 1 or 2, with the proviso that when n is 2, X may be same or different, together with a suitable inert carrier.

Furthermore, the present invention provides the novel N-substituted alanine derivatives of the above mentioned general formula, which may be used as active substances in said plant growth regulator.

DETAILED DESCRIPTION OF THE INVENTION

The present invention relates to a plant growth regulator containing as the active ingredient N-substituted alanine derivatives of the above mentioned general formula I. The N-substituted alanine derivatives of the general formula I exist in the form of isomers which are also included in the present invention.

In the compounds of the general formula I of the present invention, X as halogen atom may be for example fluorine, chlorine, bromine and iodine. R as lower alkyl may be methyl, ethyl, n-propyl, iso-propyl, n-butyl, isobutyl and tert-butyl, and as lower alkenyl, may be ethenyl, allyl, iso-propenyl, butenyl and iso-butenyl.

R as an alkali metal atom may be sodium or potassium and the amine-forming residue may be dimethylammonium, diethylammonium and triethylammonium.

Among the compounds of the general formula I, preferred compounds to be used in the present invention are those wherein X represents fluorine, chlorine or trifluoromethyl and R represents methyl, ethyl, n-propyl, isopropyl, butyl or allyl.

Preferable compounds are those of the general formula I wherein R represents a straight chain or branched chain alkyl having 1-4 carbon atoms and n is preferably 1 or 2.

More preferred compounds of the formula I are those wherein X represents halogen atom, especially chlorine or fluorine atom, or trifluoromethyl, R represents n-alkyl group having 2-4 carbon atoms and n is 1 or 2.

Most preferable compounds are:

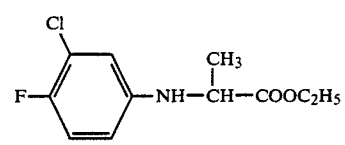
No. 11

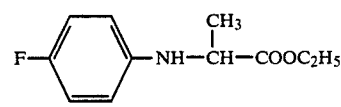
No. 14

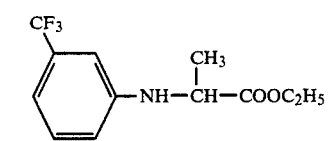
No. 17

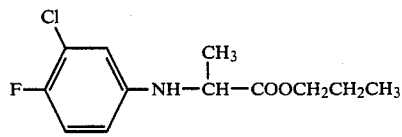
No. 26

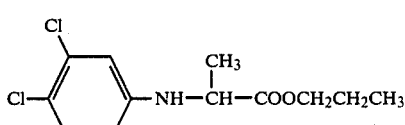
No. 30

-continued

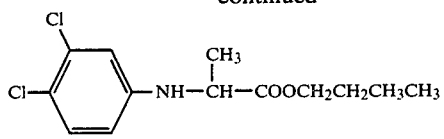

No. 32

The compounds of the general formula I to be used in the present invention include some novel compounds and also known compounds.

Therefore, the present invention relates to novel compounds of the general formula Ia:

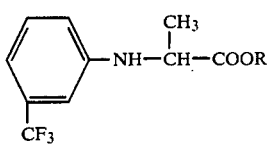

Ia wherein R represents a straight chain or branched alkyl having 1-4 carbon atoms.

Next, processes for producing the compounds of the present invention will be exemplified by the reaction formulae as follows:

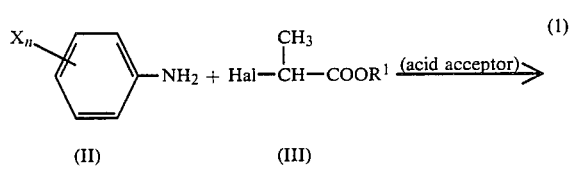

$$X_n\text{-}C_6H_4\text{-}NH_2 + Hal\text{-}CH(CH_3)\text{-}COOR^1 \xrightarrow{\text{(acid acceptor)}} \quad (1)$$

(II) (III)

$$X_n\text{-}C_6H_4\text{-}NH\text{-}CH(CH_3)\text{-}COOR^1 \quad (IV)$$

$$X_n\text{-}C_6H_4\text{-}NH\text{-}CH(CH_3)\text{-}COOR^1 \xrightarrow{MOH} \quad (2)$$

(IV)

$$X_n\text{-}C_6H_4\text{-}NH\text{-}CH(CH_3)\text{-}COOM \quad (V)$$

$$X_n\text{-}C_6H_4\text{-}NH\text{-}CH(CH_3)\text{-}COOM \xrightarrow{\text{mineral acid}} \quad (3)$$

(V)

$$X_n\text{-}C_6H_4\text{-}NH\text{-}CH(CH_3)\text{-}COOH \quad (VI)$$

$$X_n\text{-}C_6H_4\text{-}NH\text{-}CH(CH_3)\text{-}COOH \xrightarrow{NH(R^2,R^3)} \quad (4)$$

(VI)

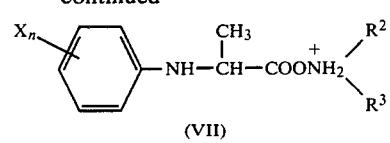

(VII)

In the above reaction formulae, X and n have the same meanings as above defined, Hal represents a halogen atom, $R^1$ represents lower alkyl, M represents an alkali metal atom and $R^2$ and $R^3$ represent each lower alkyl.

In the reaction of Reaction Formula (1), the compound (IV) of the present invention can be easily produced by heating the compound of formula (II) with the compound of formula (III) under reflux in an inert solvent in the presence of an acid acceptor such as anhydrous potassium carbonate.

In the reaction of Reaction Formula (2), the compound (V) of the present invention can be easily obtained by hydrolysis of the compound of formula (IV) with aqueous alkali metal hydroxide solution under heating.

In the reaction of Reaction Formula (3), the compound (VI) of the present invention may be easily obtained by acidifying the compound of formula (V) with a mineral acid such as hydrochloric acid to precipitate the free acid.

In the reaction of Reaction Formula (4), Compound (VI) is mixed with various kinds of amine, thereby forming, for example, the compound of formula (VII) of the present invention.

In the following, the process for producing the compounds of the present invention will be more specifically explained by showing some synthesis examples.

SYNTHESIS EXAMPLE 1

Synthesis of N-(3-chloro-4-fluorophenyl)alanine ethyl ester (Compound No. 11)

In 50 ml of acetonitrile were added 14.6 g of 3-chloro-4-fluoroaniline, 12.1 g of ethyl α-bromopropionate and 6.9 g of anhydrous potassium carbonate and the mixture was heated under reflux for 24 hrs. The reaction mixture was filtered and the filtrate was concentrated and distilled in vacuo to give 10.0 g of the captioned object compound, boiling point being 97°-100° C./0.13 mm Hg.

The compound thus obtained (Compound No. 11) was hydrolyzed by heating it with aqueous sodium hydroxide solution to give sodium salt of the carboxylic acid, the object compound (Compound No. 13). This salt was acidified with hydrochloric acid to precipitate the free carboxylic acid of the object compound (Compound No. 12).

In the same manner as in Synthesis Example 1, various compounds of the present invention as listed in Table 1 were produced.

The same compound number as indicated in Table 1 will be referred to in the following formulation examples and the test examples.

TABLE 1

Compounds of the formula:

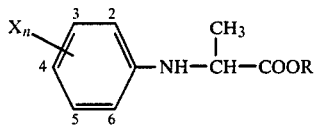

| Compound No. | $X_n$ | R | Boiling point (°C./mm Hg) |
|---|---|---|---|
| 1 | 2-Cl | $C_2H_5$ | 104–106/0.35 |
| 2 | 3-Cl | $C_2H_5$ | 98–100/0.25 |
| 3 | 4-Cl | $C_2H_5$ | 89/0.34 |
| 4 | 2,3-$Cl_2$ | $C_2H_5$ | 135/2.0 |
| 5 | 2,4-$Cl_2$ | $C_2H_5$ | 106–107/0.35 |
| 6 | 3,4-$Cl_2$ | $C_2H_5$ | 124/0.4 |
| 7 | 3,5-$Cl_2$ | $C_2H_5$ | 116/0.28 |
| 8 | 2,5-$Cl_2$ | $C_2H_5$ | — |
| 9 | 2,6-$Cl_2$ | $C_2H_5$ | 102/0.4 |
| 10 | 3,4-$Cl_2$ | Na | — |
| 11 | 3-Cl, 4-F | $C_2H_5$ | 97–100/0.13 |
| 12 | 3,4-$Cl_2$ | H | 148–149° C. (m.p.) |
| 13 | 3-Cl, 4-F | Na | — |
| 14 | 4-F | $C_2H_5$ | 84/0.18 |
| 15 | 4-Br | $C_2H_5$ | 114–115.5/0.16 |
| 16 | 4-I | $C_2H_5$ | 33–35° C. (m.p.) |
| 17 | 3-$CF_3$ | $C_2H_5$ | 93.5/0.2 |
| 18 | 4-$CF_3$ | $C_2H_5$ | 32–34° C. (m.p.) |
| 19 | H | $CH_3$ | |
| 20 | H | $-CH_2CH=CH_2$ | |
| 21 | H | $-CH_2CH_2CH_3$ | |
| 22 | H | $-CH(CH_3)_2$ | |
| 23 | H | $-CH_2CH_2CH_2CH_3$ | |
| 24 | 3-Cl, 4-F | $-CH_3$ | 89.5/0.12 |
| 25 | 3-Cl, 4-F | $-CH_2CH=CH_2$ | 113.5/0.17 |
| 26 | 3-Cl, 4-F | $-CH_2CH_2CH_3$ | 99/0.1 |
| 27 | 3-Cl, 4-F | $-CH(CH_3)_2$ | 60.5–61.3° C. (m.p.) |
| 28 | 3-Cl, 4-F | $-CH_2CH_2CH_2CH_3$ | 103.5–105.5/0.1 |
| 29 | 3,4-$Cl_2$ | $-CH_2CH=CH_2$ | 131.7/0.2 |
| 30 | 3,4-$Cl_2$ | $-CH_2CH_2CH_3$ | 110/0.16 |
| 31 | 3,4-$Cl_2$ | $-CH(CH_3)_2$ | 85.7–86.8° C. (m.p.) |
| 32 | 3,4-$Cl_2$ | $-CH_2CH_2CH_2CH_3$ | 125.6/0.16 |
| 33 | 3-$CF_3$ | $-CH_2CH=CH_2$ | |
| 34 | 3-$CF_3$ | $-CH_2CH_2CH_3$ | |
| 35 | 3-$CF_3$ | $-CH(CH_3)_2$ | |
| 36 | 3-$CF_3$ | $-CH_2CH_2CH_2CH_3$ | |

Next, for application of the compounds of the present invention as the suckers controlling agent for tobacco or young shoots inhibiting agent for woody plants, there is no specific limitation in the formulations or preparations, however, emulsion is preferred. Various carriers may be mixed with the compounds of the present invention to prepare the emulsion formulation, for example solvents such as benzene, toluene, xylene and the like. An emulsion which is prepared by mixing the compound of the present invention with said solvent and various surface active agents may be used as such, or preferably after dilution with water to a desired concentration.

The use amount of the compound of the present invention, which depends upon the purpose of application, species of tobacco or woody plants to be treated, timing of application and other conditions for treatment, may generally be from 1 to 10,000 ppm, preferably is from 1,000–5,000 ppm.

In the following, concrete examples of formulation will be shown, but the present invention is not limited to these examples. The "part" mentioned in the following formulation examples means "part by weight".

FORMULATION EXAMPLE 1

| | |
|---|---|
| Invention Compound No. 11 | 20 parts |
| Xylene | 70 parts |
| Sorpol ® 2680 | 10 parts |
| (Trade name of a mixture of nonionic surface agent and anionic surface agent; product of Toho Chemical Co.) | |

The above components are uniformly mixed to prepare an emulsion. This is diluted 20–2000 times with water upon application.

| | |
|---|---|
| Invention Compound No. 30 | 25 parts |
| Toluene | 65 parts |
| Sorpol ® 2680 | 10 parts |
| (Trade name of a mixture of nonionic surface agent and anionic surface agent; product of Toho Chemical Co.) | |

The above components are well mixed with each other to prepare an emulsion. This is diluted 25–2500 times with water upon application.

There is no limitation in the concentration of the compound of the present invention in the emulsion, but a concentration of 1–70% by weight, preferably 5–50% by weight may be employed.

In the following, the present invention will be explained in more detail by referring to Reference Examples wherein auxin activities of the compounds of the present invention are determined and Test Examples wherein young shoots controlling activity on woody plants and suckers controlling activity on tobacco of the compounds of the present invention are measured.

REFERENCE EXAMPLE 1

Test of auxin activity

Each 10 grains of paddy rice seeds and 10 ml of a solution containing the test compound at a prescribed concentration were placed in a petri dish of a diameter of 7 cm. The dish was kept at 25° C. in dark condition for 10 days to sprout, and average root length at this time was measured, which was compared with the average root length obtained from seeds in a dish containing only water. The results are expressed by comparison with untreated plants, the value of which is referred to as 100 are listed in Table 2. The smaller the values, the stronger the auxin activities. Representative, known compounds having auxin activity 2,4-D (trade name) and NAA (trade name) were also tested as control compounds.

The active substance of 2,4-D is 2,4-dichlorophenoxyacetic acid (hereinafter referred to as Control Compound A) and that of NAA is α-naphthalen-acetic acid (hereinafter referred to as Control Compound B).

TABLE 2

| | Comparison value of average root length Concentration of active substance | | | |
|---|---|---|---|---|
| Compound No. | 200 ppm | 100 ppm | 20 ppm | 5 ppm |
| 1 | 0 | 0 | 4 | 9 |
| 2 | 0 | 0 | 4 | 17 |
| 3 | 0 | 0 | 4 | 26 |
| 4 | 0 | 17 | 55 | 95 |
| 5 | 0 | 2 | 4 | 23 |
| 6 | 0 | 6 | 24 | 54 |
| 7 | 0 | 10 | 11 | 73 |
| 8 | 0 | 0 | 4 | 11 |
| 9 | 0 | 14 | 20 | 83 |
| 10 | 0 | 0 | 9 | 33 |
| 11 | 0 | 0 | 0 | 11 |

TABLE 2-continued

| Compound No. | Comparison value of average root length Concentration of active substance | | | |
|---|---|---|---|---|
| | 200 ppm | 100 ppm | 20 ppm | 5 ppm |
| 12 | 0 | 0 | 11 | 19 |
| 13 | 0 | 0 | 18 | 37 |
| 14 | 0 | 0 | 5 | 11 |
| 15 | 0 | 0 | 18 | 11 |
| 16 | 0 | 0 | 7 | 11 |
| 17 | 0 | 0 | 5 | 32 |
| 18 | 0 | 0 | 62 | 116 |
| 19 | 0 | 4 | 26 | 57 |
| 20 | 0 | 0 | 13 | 48 |
| 21 | 0 | 0 | 11 | 42 |
| 22 | 0 | 13 | 33 | 63 |
| 23 | 0 | 2 | 4 | 32 |
| 24 | 0 | 0 | 0 | 17 |
| 25 | 0 | 0 | 0 | 13 |
| 26 | 0 | 0 | 0 | 9 |
| 27 | 0 | 0 | 11 | 67 |
| 28 | 0 | 0 | 4 | 17 |
| 29 | 0 | 4 | 11 | 32 |
| 30 | 0 | 0 | 0 | 22 |
| 31 | 0 | 7 | 13 | 48 |
| 32 | 0 | 9 | 15 | 22 |
| Control Compound A | 0 | 0 | 0 | 8 |
| Control Compound B | 0 | 0 | 2 | 20 |

As is clearly seen in the results of Table 2, the compounds of the present invention exhibit strong auxin activity.

REFERENCE EXAMPLE 2

Spraying test on yound plant of tomato

When a young plant of tomato had reached to 4-leaf stage, an emulsion containing a test compound at prescribed concentration was uniformly sprayed on the stems and the leaves. Degree of malformation was assessed 5 days after the treatment. The result is indicated in Table 3. The symbols in Table 3 are expressed by the following criterion.

: considerable malformation
Δ: medium malformation
±: low or no malformation

TABLE 3

| Compound No. | Concentration of active substance | | |
|---|---|---|---|
| | 200 ppm | 50 ppm | 10 ppm |
| 1 | Δ | Δ | ± |
| 6 | Δ | ± | ± |
| 11 | ± | ± | ± |
| 14 | ± | ± | ± |
| 17 | ± | ± | ± |
| 26 | Δ | ± | ± |
| 28 | Δ | ± | ± |
| 30 | Δ | ± | ± |
| Control Compound A | | | |
| Control Compound B | | | |

As is clearly seen in Table 3, the compounds of the present invention, which have strong auxin activity on the same level as 2,4-D (Control Compound A) and NAA (Control Compound B), as shown in Reference Example 1, showed far lower occurrence of malformation.

Next, practical use of the compounds of the present invention as plant growth regulator, i.e. young shoots controlling action on woody plants and suckers controlling activity on tobacco were tested.

Controlling young shoots of woody plants is sometimes very important, for instance trees in a green zone are pruned once or several times a year in order to maintain the shapes and beauties of the trees. Furthermore, excess growth of new branches of fruit trees is often unfavorable. The compounds of the present invention effectively control new buds in these cases.

Control of suckers of tobacco is also very important. In order to maintain high quality of tobacco leaves, the top of the plant is in general pinched at the beginning of anthesis. However, suckers may grow after the top pinching, which deteriorates the quality of tobacco leaves, if it is allowed to stand untreated. Controlling suckers is very important to maintain the quality. The compounds of the present invention can effectively control suckers in such a case. In the following, the invention will be concretely explained by test examples.

TEST EXAMPLE 1

Test on control of new buds of woody plants

A mandarin orange tree (the height is ca. 50 cm) planted in each pot of a diameter of about 16 cm was uniformly sprayed with emulsion of test compound at a prescribed concentration on the stems and the leaves before sprout in spring. Sprout of new buds and phytotoxicity were assessed 2 months after the treatment. The result is indicated in Table 4.

TABLE 4

| Compound No. | Concentration of test compound (ppm) | Sprout of new buds | Phytotoxicity |
|---|---|---|---|
| 1 | 2000 | none-low | none-low |
| 6 | " | none | none-low |
| 11 | " | none | none |
| 14 | " | none | none |
| 17 | " | none | none |
| 26 | " | none | none |
| 28 | " | none | none |
| 30 | " | none | none |
| Control Compound A | " | none | high |
| Control Compound B | " | slight-little | moderate |
| No treatment | — | many | none |

As is clearly seen in Table 4, the compounds of the present invention showed sufficient activity for controlling sprout of new buds while showing low phytotoxicity.

TEST EXAMPLE 2

Test on control of suckers of tobacco

Tobacco plants to be tested (variety: Shiro Enshu) were pinched at the beginning of anthesis and the pinched portions were uniformly sprayed with a diluted emulsion of the compounds of the present invention at the prescribed concentrations. Each 10 plants were tested for each treatment. After 2 weeks from the treatment, average weight of dry suckers per plant of tobacco was measured and phytotoxicity was also assessed. It is known that 2,4-D and NAA can not be practically used due to their high phytotoxicity.

The result is shown in Table 5.

TABLE 5

| Compound No. | Concentration of test compound (ppm) | Weight of dry suckers (g/plant) | Phytotoxicity |
|---|---|---|---|
| 11 | 3,000 | 0.60 | none |
| | 2,000 | 0.70 | none |
| | 1,000 | 1.83 | none |
| 14 | 3,000 | 0.94 | none |
| | 2,000 | 1.01 | none |

TABLE 5-continued

| Compound No. | Concentration of test compound (ppm) | Weight of dry suckers (g/plant) | Phytotoxicity |
|---|---|---|---|
| | 1,000 | 2.37 | none |
| 17 | 3,000 | 0.80 | none |
| | 2,000 | 0.92 | none |
| | 1,000 | 2.23 | none |
| 26 | 3,000 | 0.53 | none |
| 30 | 3,000 | 0.51 | none |
| 32 | 3,000 | 0.48 | none |
| Control Compound A | 3,000 | 0.42 | high |
| Control Compound B | 3,000 | 1.06 | high–medium |
| No treatment | — | 4.66 | — |

As is clearly seen in Table 5, the compounds of the present invention can effectively control growth of suckers while showing no phytotoxicity. Therefore, the compounds of the present invention are of sufficiently practical use as the suckers controlling agent for tobacco.

What is claimed is:

1. A process for controlling the growth of suckers on a tobacco plant which comprises contacting the plant with a suckers controlling amount of a plant growth regulator comprising an N-substituted alanine derivative of the formula:

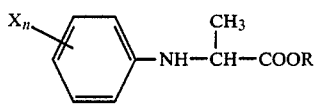

wherein X represents halogen atom or trifluoromethyl, R represents hydrogen, straight chain or branched chain alkyl having 1–4 carbon atoms, alkenyl having 2–4 carbon atoms, an alkali metal atom or amine-forming residue, and n is zero or an integer of 1 or 2, with the proviso that when n is 2, X may be the same or different.

2. A process of claim 1 wherein said plant growth regulator further comprises an inert carrier.

3. A process of claim 1 wherein R is a straight chain or branched chain alkyl having 1 to 4 carbon atoms and n is 2.

4. A process of claim 1 wherein X is trifluoromethyl, n is 1 and R is a straight chain or branched chain alkyl having 1–4 carbon atoms.

5. A process of claim 2 wherein the N-substituted alanine derivative comprises 1,000 to 5,000 ppm of said plant growth regulator.

6. Process for controlling suckers of tobacco by treating the vicinity of pinched portions of a plant with a suckers controlling amount of the plant growth regulator according to claim 1.

7. Process according to claim 1, wherein the vicinity of pinched portions of tobacco is treated with a solution containing the plant growth regulator in a concentration of 1,000–5,000 ppm to control suckers.

8. The process of claim 1 wherein the N-substituted alanine derivatives has the formula:

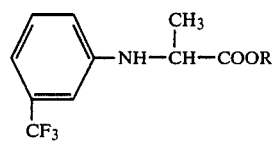

wherein R represents straight chain or branched chain alkyl of 1-4 carbon atoms.

9. The process of claim 1 wherein the N-substituted alanine derivative has the formula:

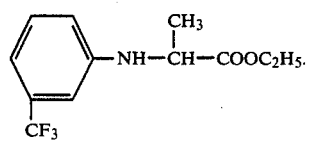

10. The process of claim 1 wherein the N-substituted alanine derivative has the formula:

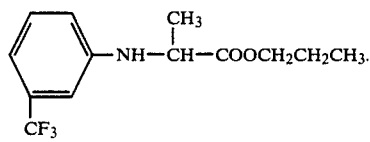

11. The process of claim 1 wherein the N-substituted alanine derivative has the formula:

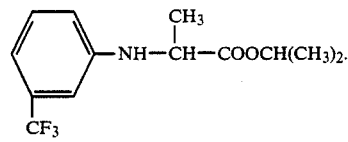

12. The process of claim 1 wherein the N-substituted alanine derivative has the formula:

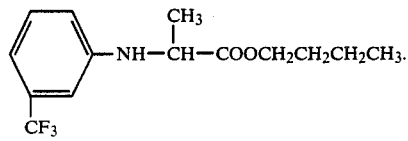

13. The process of claim 1 wherein the N-substituted alanine derivative is present in the plant growth regulator an amount of 1,000 to 5,000 ppm.

* * * * *